(12) United States Patent
Jones et al.

(10) Patent No.: US 6,193,286 B1
(45) Date of Patent: Feb. 27, 2001

(54) DEVICE AND METHOD FOR CONNECTING A FLUID CONDUIT TO A RECEIVING FITTING

(75) Inventors: Brian A. Jones, South Jordan; Nathan L. Porter, Kaysville; Curtis Kelly, Payson, all of UT (US)

(73) Assignee: Selerity Technologies Inc., Salt Lake City, UT (US)

( * ) Notice: Subject to any disclaimer, the term of this patent is extended or adjusted under 35 U.S.C. 154(b) by 0 days.

(21) Appl. No.: 09/258,173

(22) Filed: Feb. 25, 1999

Related U.S. Application Data

(60) Provisional application No. 60/076,112, filed on Feb. 27, 1998.

(51) Int. Cl.[7] .................................................. F16L 17/00
(52) U.S. Cl. .......................... 285/354; 285/353; 285/343
(58) Field of Search ..................................... 285/342, 343, 285/353, 357, 332, 375, 354

(56) References Cited

U.S. PATENT DOCUMENTS

| | | | |
|---|---|---|---|
| 4,313,828 | * | 2/1982 | Brownlee .............................. 285/109 |
| 4,451,364 | * | 5/1984 | Higgins et al. ...................... 285/109 |
| 4,669,756 | | 6/1987 | Cassaday et al. . |
| 4,732,672 | | 3/1988 | Kiang et al. . |
| 4,991,883 | | 2/1991 | Worden . |
| 5,163,215 | | 11/1992 | Ledford, Jr. . |
| 5,163,722 | | 11/1992 | Worden . |
| 5,188,730 | | 2/1993 | Kronwald . |
| 5,234,235 | * | 8/1993 | Worden ................................ 285/342 |
| 5,525,303 | | 6/1996 | Ford et al. . |
| 5,582,723 | | 12/1996 | Boone et al. . |
| 5,595,406 | * | 1/1997 | Warchol .............................. 285/319 |
| 5,601,785 | * | 2/1997 | Higdon ................................ 422/103 |
| 6,102,449 | * | 8/2000 | Welsh .................................. 285/354 |

* cited by examiner

Primary Examiner—Lynne H. Browne
Assistant Examiner—Aaron Dunwoody
(74) Attorney, Agent, or Firm—Holland & Hart, LLP

(57) ABSTRACT

A fitting provides a means of making a union between a tube and a female fitting with low dead volume and without the use of tools. The fitting is comprised of a tube member that is pressed into the female fitting to automatically remove dead volume. The tube member is pressed into the fitting by a spring with the appropriate tension to hold the tube member against the expected pressure. The fitting also is comprised of a two piece nut assembly. The forward nut compresses a ferrule to create the high-pressure seal. The rearward nut is attached to the forward nut and provides compression and a holding means for the spring.

20 Claims, 3 Drawing Sheets

DEVICE AND METHOD FOR CONNECTING A FLUID CONDUIT TO A RECEIVING FITTING

This application claims the benefit of U.S. Provisional Application No. 60/076,112, filed Feb. 27 1998.

TECHNICAL FIELD OF THE INVENTION

This invention relates in general to fittings and, more specifically, to devices and methods for connecting fluid conduits (e.g., tubes) to receiving fittings. This invention is particularly applicable to the field of chromatography.

BACKGROUND OF THE INVENTION

A variety of tube fittings that are useful in the field of chromatography are commercially available. Most of these fittings employ a ferrule system that is swaged onto the tube.

One known design for making what is referred to as a "low dead volume connection" is called a "slip-free connector". With this connector, the depth of tubing penetration into a receiving fitting, and the compression force on a polymeric sealing ferrule, can be independently adjusted through the use of a two-part nut. The design of this connector is described as part of a chromatographic cartridge in U.S. Pat. No. 5,582,723. Unfortunately, this design can be difficult to use if the back part of the nut is too tight prior to installation into a receiving fitting. When this occurs, the tubing bottoms out in the receiving fitting and prevents compression of the sealing ferrule. Continued tightening of the "slip-free connector" without first loosening the back part of the nut eventually causes damage to the tubing or the receiving fitting.

A problem with tubing connection fittings in general is interchangeability from manufacturer to manufacturer. Different manufacturers use different penetration depths from the end of the sealing ferrule to the bottom of the receiving fitting, and penetration depths can even vary among different products from the same manufacturer. Because these fittings are assembled with the ferrule permanently swaged onto the tubing, using an already assembled tube in a different fitting can cause problems. If the tube extends too far past the end of the swaged-on ferrule the tube will bottom out in the fitting, which can make it difficult to get an adequate seal, or can damage the fitting. Conversely, if the tube does not extend far enough beyond the swaged-on ferrule the space not filled by the tubing results in dead volume. Use of the "slip-free connector" described above addresses the problem with interchangeability of fittings from one manufacturer to another, but as described above it can be difficult to use.

It is generally difficult to obtain reliable seals on $\frac{1}{32}\Delta$ tubing, which is common in chromatography applications. This size of tubing is typically thin-walled and, as the ferrule is tightened, the tubing can be deformed to the point where a reliable seal cannot be achieved. Continued tightening only aggravates this problem, and eventually the tubing is crimped closed or the sealing nut breaks.

U.S. Pat. No. 4,669,756 describes the use of a spring-loaded fitting to controllably force the ends of soft plastic tubing together to make a seal. In this case the ferrules are attached to the tubing ends and then pressed together with a spring. This is claimed to work with soft tubing, where deformation of the tubing ends occurs as they form the seal. As a result, this device has limited capability to seal to high pressure.

In addition, U.S. Pat. No. 4,732,672 describes a means of quickly mounting high-pressure liquid chromatography columns by using spring tension to force tubing into the end fittings of the columns. This same spring tension produces force on the sealing ferrule as well. The device is large and cumbersome, however, and the force on the tubing is achieved by a tight bend through a channel to a perpendicular dimension. Thin-walled tubing would collapse under forces required to keep it from being pushed out of the end fitting during high-pressure use. Also, the fact that the same spring is used to provide the tube holding force and the ferrule compression force means there is no independent control of these parameters.

U.S. Pat. Nos. 4,991,883, 5,163,722, and 5,163,215 describe spring-loaded connection devices wherein controlled pressure is applied to the sealing ferrule. This provides a constant sealing force on the ferrule member but does not provide for automatic bottoming out of the tubing in the receiving fitting.

U.S. Pat. Nos. 5,188,730 and 5,525,303 describe multiple-part connection devices that provide for dead volume removal by adjustment of a tubing member. These are similar to the "slip-free connection" device described earlier, and they suffer from the same problems, namely, that the rear supporting threaded member can be prematurely tightened, causing the tubing to prematurely bottom in the receiving fitting. This causes unreliable sealing and potential damage to the tubing or the receiving fitting.

The failure of current connection fittings to provide a reliable means of sealing tubing in a receiving fitting while automatically removing dead volume shows the need for a fitting that provides a simple, convenient yet robust means of connecting tubing to a receiving fitting while automatically removing dead volume in a small easy to use package.

SUMMARY OF THE INVENTION

A device in accordance with this invention connects a fluid conduit, such as a tube, to a threaded receiving fitting. The device includes a retention member (e.g., a washer) that attaches to the fluid conduit, and a fitting member that has a first threaded end that connects to the threaded receiving fitting and a second, opposing threaded end with a substantially axial cavity. The first threaded end has a substantially axial hole extending through to the cavity in the second threaded end that receives the fluid conduit so the conduit extends through the cavity and hole with the retention member proximate an interior end of the cavity and an end of the fluid conduit extending beyond the first threaded end. A deformable member (e.g., a sealing ferrule) seals the connection to the receiving fitting. The deformable member has a substantially axial hole through it that receives the fluid conduit so that the deformable member abuts the first threaded end of the fitting member and the end of the fluid conduit extends beyond the deformable member into the receiving fitting. A bias member (e.g., a spring) is coaxially mounted on the fluid conduit with a first end of the bias member abutting the retention member in the cavity in the second threaded end of the fitting member. A cap member has a threaded cavity that connects to the second threaded end of the fitting member so that a second end of the bias member abuts an interior end of the threaded cavity. The cap member also has a substantially axial hole through it that receives the fluid conduit.

In another embodiment of this invention, a fluid conduit is connected to a receiving fitting by positioning a deformable member coaxially about the fluid conduit. The fluid conduit is then biased against the receiving fitting and, independent of the act of biasing the fluid conduit, the deformable member is driven into the receiving fitting to seal the fitting.

DETAILED DESCRIPTION OF THE ILLUSTRATED EMBODIMENTS

Figure 1:
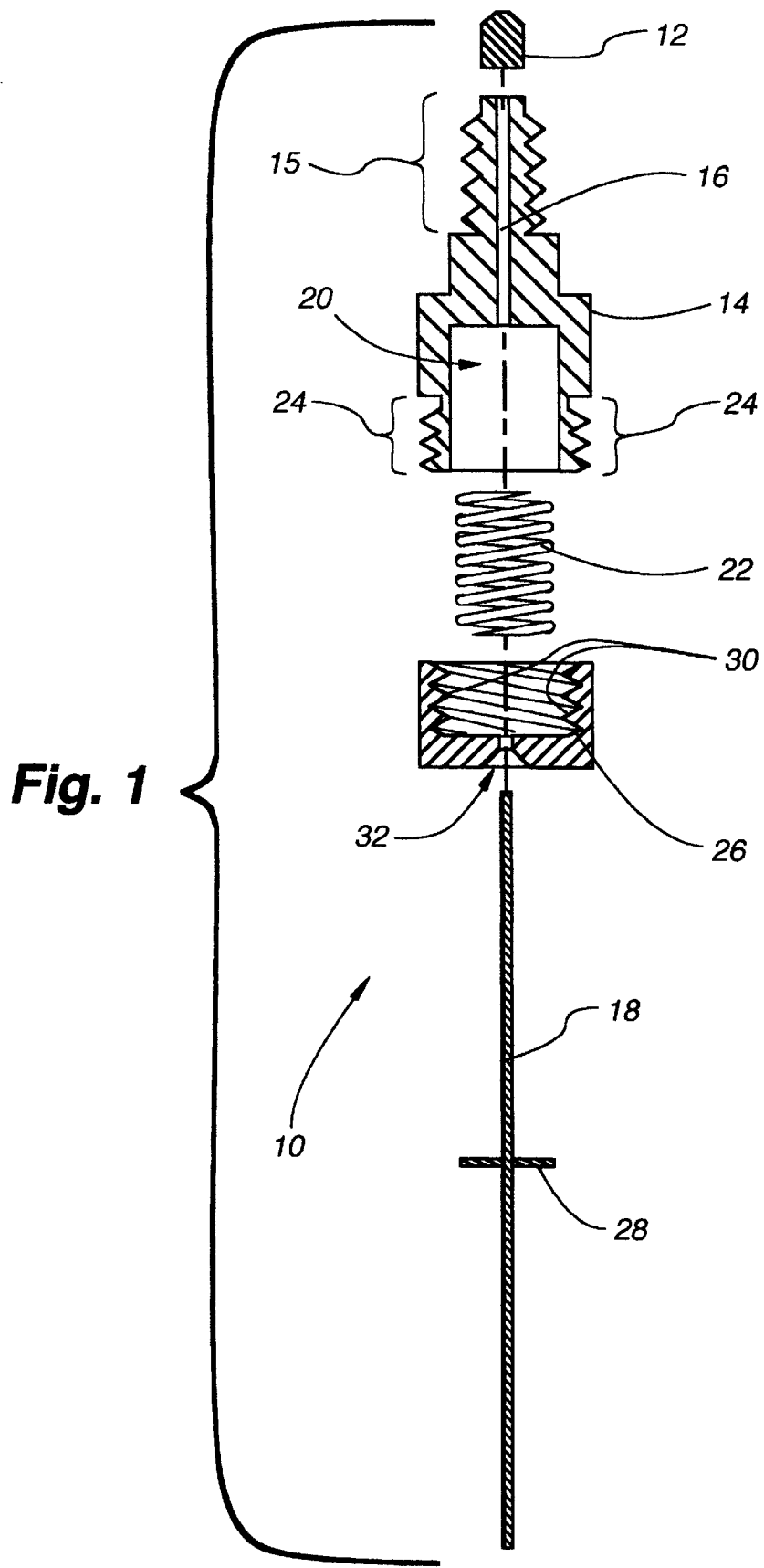
FIG. 1 is a sectional view illustrating a fitting constructed in accordance with this invention.

As shown in FIG. 1, a fitting 10 constructed in accordance with this invention includes a sealing ferrule 12 preferably made using graphite/vespel, although any deformable material, such as metal, will work. A front nut 14 has threads 15 for screwing into a receiving fitting (see FIG. 3), a channel 16 for a tube 18 to slide through, a recess 20 for holding a spring 22, and threads 24 for attachment of an end cap nut 26. The spring 22 is sized to provide appropriate tension on a washer 28 for the pressure under which the fitting 10 is to operate. The end cap nut 26 has a threaded region 30 to attach to the front nut 14 and a hole 32 to allow free movement of the tube 18 down its center.

It will be understood by those having skill in the technical field of this invention that while the invention will be described with respect to a tube for conducting gasses, the invention is also applicable to other fluid conduits conducting other fluids, including both gasses and liquids.

Figure 2:
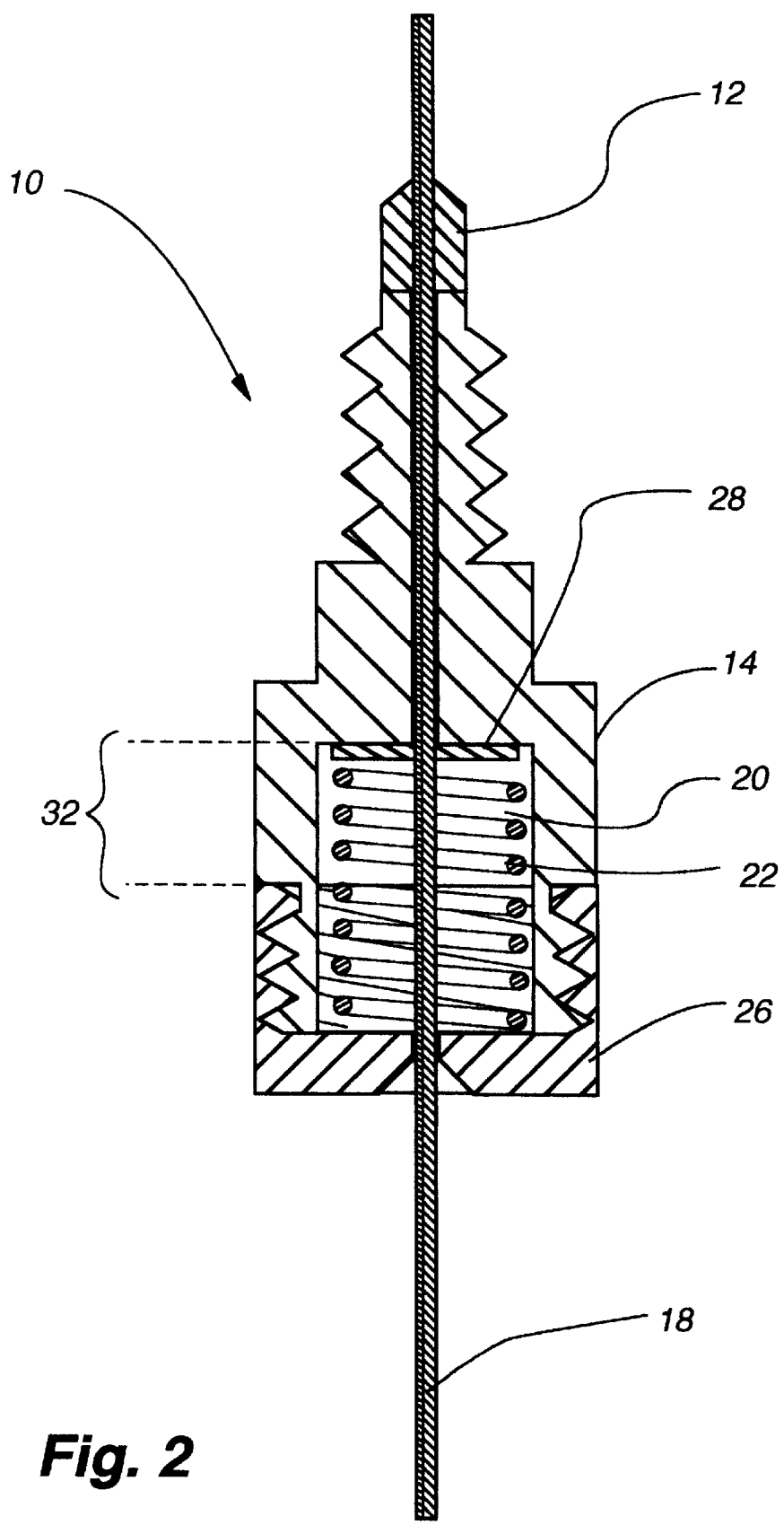
FIG. 2 is a sectional view illustrating the fitting of FIG. 1 in its assembled form.

As shown in FIG. 2, the washer 28 of the fitting 10 is attached to the tube 18 with silver solder, or any other means that will provide a secure connection. Of course, other attachments besides the washer 28 could be used. As the fitting 10 is assembled, the tube 18 and washer 28 together slide through the front nut 14, and the spring 22 slides onto the tube 18 and against the washer 28. At this point, the end cap nut 26 is screwed onto the front nut 14 until it stops. A predetermined depth 32 for the cavity 20 in the front nut 14 is used so that tightening the end cap nut 26 provides the appropriate amount of compression on the spring 22 for the expected pressure to be sealed against. After the fitting 10 is assembled, the ferrule 12 is slid on to the tube 18 prior to installing the fitting 10 into the receiving fitting (see FIG. 3).

Figure 3:
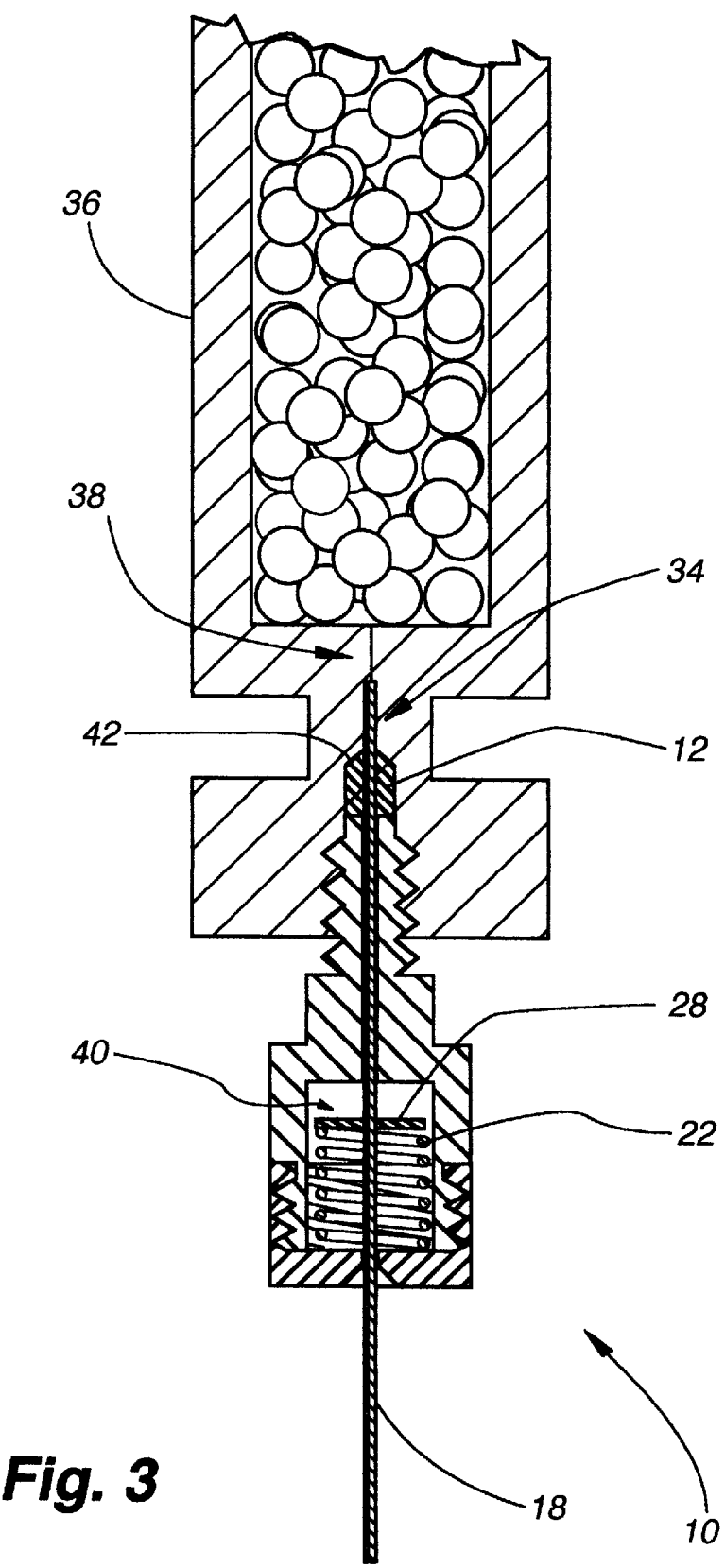
FIG. 3 is a sectional view illustrating the fitting of FIG. 1 assembled and connected to a receiving fitting.

As shown in FIG. 3, the fitting 10 is installed in a receiving fitting 34 of a chromatography column 36. Of course, the present invention is applicable to any receiving fitting, not just those associated with a chromatography column.

The fitting 10 is tightened into the receiving fitting 34, causing the tube 18 to bottom out against webbing 38 in the receiving fitting 34. As the tube 18 bottoms out, it is pushed back, causing the spring 22 to be compressed by the washer 28 attached to the tube 18. Compression of the spring 22 leaves a small space 40 in the front nut cavity 20. This compressing action keeps the tube 18 tight against the webbing 38, thus eliminating any potential dead volume. As the fitting 10 is threaded further into the receiving fitting 34, the ferrule 12 comes in contact with the conical portion 42 of the receiving fitting 34. The ferrule 12 is compressed until a leak-tight seal is made. With the spring 22 supporting the tube 18, the seal is stable to pressures of approximately 10,000 psi.

Although this invention has been described with reference to particular embodiments, the invention is not limited to these described embodiments. Rather, the invention is limited only by the appended claims, which include within their scope all equivalent devices and methods that operate according to the principles of the invention as described.

What is claimed is:

1. A device for connecting a fluid conduit to a threaded receiving fitting, the device comprising:

a retention member for attachment to the fluid conduit;

a fitting member having a first threaded end for connection to the threaded receiving fitting and a second, opposing threaded end with a substantially axial cavity therein, the first threaded end having a substantially axial hole therein extending therethrough to the cavity in the second threaded end for receiving the fluid conduit such that the conduit extends through the cavity in the second threaded end and the hole in the first threaded end with the retention member proximate an interior end of the cavity and an end of the fluid conduit extending beyond the first threaded end;

a deformable member, different than the retention member, for sealing a connection to the receiving fitting, the deformable member having a substantially axial hole therethrough for receiving the fluid conduit such that the deformable member abuts the first threaded end of the fitting member and the end of the fluid conduit extends beyond the deformable member into the receiving fitting;

a bias member for coaxial mounting on the fluid conduit with a first end of the bias member abutting the retention member in the cavity in the second threaded end of the fitting member; and a cap member having a threaded cavity therein for connection to the second threaded end of the fitting member such that a second end of the bias member abuts an interior end of the threaded cavity, the cap member having a substantially axial hole therethrough for receiving the fluid conduit.

2. The device of claim 1 wherein the fluid conduit comprises a tube.

3. The device of claim 1 wherein the threaded receiving fitting is associated with a chromatography column.

4. The device of claim 1 wherein the retention member comprises a washer.

5. The device of claim 1 wherein the deformable member comprises a ferrule.

6. The device of claim 1 wherein the bias member comprises a spring.

7. The device of claim 1 wherein the cap member comprises an end cap nut.

8. A device for connecting a fluid conduit to a threaded receiving fitting, the device comprising:

a retention member for attachment to the fluid conduit using silver solder;

a fitting member having a first threaded end for connection to the threaded receiving fitting and a second, opposing threaded end with a substantially axial cavity therein, the first threaded end having a substantially axial hole therein extending therethrough to the cavity in the second threaded end for receiving the fluid conduit such that the conduit extends through the cavity in the second threaded end and the hole in the first threaded end with the retention member proximate an interior end of the cavity and an end of the fluid conduit extending beyond the first threaded end;

a deformable member, different than the retention member for sealing a connection to the receiving fitting, the deformable member having a substantially axial hole therethrough for receiving the fluid conduit such that the deformable member abuts the first threaded end of the fitting member and the end of the fluid conduit extends beyond the deformable member into the receiving fitting;

a bias member for coaxial mounting on the fluid conduit with a first end of the bias member abutting the retention member in the cavity in the second threaded end of the fitting member; and a cap member having a threaded cavity therein for connection to the second threaded end of the fitting member such that a second end of the bias member abuts an interior end of the threaded cavity, the cap member having a substantially axial hole therethrough for receiving the fluid conduit.

9. The device of claim 1 wherein the deformable member is made using graphite/vespel.

10. The device of claim 1 wherein the deformable member is made using a metal.

11. The device of claim 1 wherein the fluid conduit conducts gasses.

12. A male fitting for connecting a tube to a chromatography column having a threaded female fitting, the male fitting comprising:

a washer for attachment to the tube;

a male fitting member having a first threaded end for connection to the female fitting of the chromatography column and a second, opposing threaded end with an axial cavity therein, the first threaded end having an axial hole therein extending therethrough to the cavity in the second threaded end for receiving the tube such that the tube extends through the cavity in the second threaded end and the hole in the first threaded end with the washer proximate an interior end of the cavity and an end of the tube extending beyond the first threaded end;

a sealing ferrule for sealing a connection to the female fitting, the sealing ferrule having an axial hole therethrough for receiving the tube such that the sealing ferrule abuts the first threaded end of the male fitting member and the end of the tube extends beyond the sealing ferrule into the female fitting;

a spring for coaxial mounting on the tube with a first end of the spring abutting the washer in the cavity in the second threaded end of the male fitting member; and a cap member having a threaded cavity therein for connection to the second threaded end of the male fitting member such that a second end of the spring abuts an interior end of the threaded cavity, the cap member having an axial hole therethrough for receiving the tube.

13. A male fitting for connecting a tube to a chromatography column having a threaded female fitting the male fitting comprising:

a washer for attachment to the tube using silver solder;

a male fitting member having a first threaded end for connection to the female fitting of the chromatography column and a second, opposing threaded end with an axial cavity therein, the first threaded end having an axial hole therein extending therethrough to the cavity in the second threaded end for receiving the tube such that the tube extends through the cavity in the second threaded end and the hole in the first threaded end with the washer proximate an interior end of the cavity and an end of the tube extending beyond the first threaded end;

a sealing ferrule for sealing a connection to the female fitting the sealing ferrule having an axial hole therethrough for receiving the tube such that the sealing ferrule abuts the first threaded end of the male fitting member and the end of the tube extends beyond the sealing ferrule into the female fitting;

a spring for coaxial mounting on the tube with a first end of the spring abutting the washer in the cavity in the second threaded end of the male fitting member; and a cap member having a threaded cavity therein for connection to the second threaded end of the male fitting member such that a second end of the spring abuts an interior end of the threaded cavity, the cap member having an axial hole therethrough for receiving the tube.

14. The male fitting of claim 12 wherein the sealing ferrule is made using graphite/vespel.

15. The male fitting of claim 12 wherein the sealing ferrule is made using a metal.

16. The male fitting of claim 12 wherein the tube conducts gasses.

17. A method for connecting a fluid conduit to a receiving fitting, the method comprising:

positioning a deformable member coaxially about the fluid conduit;

attaching a retention member, different than the deformable member to the fluid conduit;

biasing the retention member so as to bias the fluid conduit against the receiving fitting; and independent of the act of biasing the retention member, driving the deformable member into the receiving fitting to seal the fitting.

18. The method of claim 17 wherein the act of positioning the deformable member comprises positioning a sealing ferrule coaxially about the fluid conduit.

19. The method of claim 17 wherein the act of biasing the retention member comprises:

providing a fitting member having a first threaded end with a substantially axial cavity therein and a second, opposing threaded end with a substantially axial hole therein extending therethrough to the cavity in the first threaded end;

connecting the second threaded end of the fitting member to the receiving fitting;

inserting the fluid conduit through the cavity and hole in the respective first and second threaded ends of the fitting member so the retention member is proximate an interior end of the cavity and an end of the fluid conduit extends beyond the first threaded end;

coaxially mounting a bias member on the fluid conduit with a first end of the bias member abutting the retention member in the cavity in the second threaded end of the fitting member;

connecting a cap member having a threaded cavity therein to the second threaded end of the fitting member such that a second end of the bias member abuts an interior end of the threaded cavity; and inserting the fluid conduit through a substantially axial hole in the cap member.

20. The method of claim 17 wherein the act of driving the deformable member into the receiving fitting comprises:

providing a fitting member having a first threaded end with a substantially axial cavity therein and a second, opposing threaded end with a substantially axial hole therein extending therethrough to the cavity in the first threaded end;

positioning the deformable member so it abuts the second threaded end of the fitting member; and connecting the second threaded end of the fitting member to the receiving fitting so as to drive the deformable member into the receiving fitting to seal the fitting.

* * * * *